United States Patent [19]

Wilkinson

[11] Patent Number: 4,909,254

[45] Date of Patent: Mar. 20, 1990

[54] PHOTOTHERAPY OF SKIN WOUNDS

[75] Inventor: Frank J. Wilkinson, Mulgoa, Australia

[73] Assignee: Commonwealth Scientific and Industrial Research Organization, Campbell, Australia

[21] Appl. No.: 86,077

[22] PCT Filed: Oct. 9, 1986

[86] PCT No.: PCT/AU86/00297

§ 371 Date: Aug. 5, 1987

§ 102(e) Date: Aug. 5, 1987

[87] PCT Pub. No.: WO87/02256

PCT Pub. Date: Apr. 23, 1987

[30] Foreign Application Priority Data

Oct. 9, 1985 [AU] Australia ............... PH2828

[51] Int. Cl.$^4$ ............................................. A61N 5/08
[52] U.S. Cl. ................................. 128/396; 350/1.6
[58] Field of Search .................... 128/395–398; 252/582, 588; 350/1.1, 1.6

[56] References Cited

U.S. PATENT DOCUMENTS

| | | | |
|---|---|---|---|
| 1,510,080 | 9/1924 | Murphy | 128/395 |
| 1,856,969 | 5/1932 | Reiter et al. | 128/396 |
| 2,705,290 | 11/1975 | Strutz | 250/372 |
| 2,964,427 | 12/1960 | Rheinberger et al. | 252/588 |
| 4,279,254 | 7/1981 | Boschetti et al. | 128/395 |
| 4,320,936 | 3/1982 | Sawamura | 350/1.6 |
| 4,624,259 | 11/1986 | Welt | 128/396 |

FOREIGN PATENT DOCUMENTS

| | | |
|---|---|---|
| 505720 | of 0000 | Australia . |
| 87776 | 3/1983 | Australia . |
| 1142973 | 1/1963 | Fed. Rep. of Germany . |
| 17021 | 2/1978 | Fed. Rep. of Germany . |
| 2804228 | 8/1979 | Fed. Rep. of Germany . |
| 2906511 | 8/1980 | Fed. Rep. of Germany . |
| 2244162 | 3/1974 | France . |
| 813118 | 5/1959 | United Kingdom . |

OTHER PUBLICATIONS

Motovilov, "Narrow–Band Interference Filters for the UV Region of the Spectrum"; 6/67; *Optics and Spectroscopy;* vol. 22, pp. 537, 538.

Philips Technical Review, 41, No. 718, 1983, pp. 225–238.

*Primary Examiner*—Edward M. Coven
*Assistant Examiner*—Mark S. Graham
*Attorney, Agent, or Firm*—Ladas & Parry

[57] ABSTRACT

A method and apparatus is disclosed for irradiating wounds with UV radiation from which the UVB component is substantially removed or attenuated. UV light from a mercury vapor lamp (1) is passed through a filter (2) and thence through a lens (3) which focuses the radiation onto a target region (18). The filter (2) is formed from a number of alternating layers of dielectric material of different refractive indexes.

9 Claims, 2 Drawing Sheets